US008873042B2

(12) United States Patent
Chen et al.

(10) Patent No.: US 8,873,042 B2
(45) Date of Patent: Oct. 28, 2014

(54) METHOD FOR AUTOMATICALLY CALIBRATING A RAMAN SPECTRUM DETECTION SYSTEM AND RAMAN SPECTRUM DETECTION SYSTEM

(75) Inventors: Zhiqiang Chen, Beijing (CN); Li Zhang, Beijing (CN); Yuanjing Li, Beijing (CN); Yinong Liu, Beijing (CN); Ziran Zhao, Beijing (CN); Hongqiu Wang, Beijing (CN); Dongmei Yu, Beijing (CN); Hongfeng Gai, Beijing (CN); Mingliang Li, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 0 days.

(21) Appl. No.: 13/806,168

(22) PCT Filed: Dec. 24, 2010

(86) PCT No.: PCT/CN2010/002159
§ 371 (c)(1),
(2), (4) Date: Mar. 15, 2013

(87) PCT Pub. No.: WO2011/160270
PCT Pub. Date: Dec. 29, 2011

(65) Prior Publication Data
US 2013/0162989 A1 Jun. 27, 2013

(30) Foreign Application Priority Data

Jun. 25, 2010 (CN) .......................... 2010 1 0219542

(51) Int. Cl.
*G01J 3/44* (2006.01)
*G01N 21/65* (2006.01)
*G01J 3/28* (2006.01)
*G01N 21/27* (2006.01)

(52) U.S. Cl.
CPC ............... *G01N 21/65* (2013.01); *G01J 3/4412* (2013.01); *G01J 3/28* (2013.01); *G01N 21/274* (2013.01); *G01J 3/44* (2013.01)

USPC ......................................................... 356/301

(58) Field of Classification Search
USPC ............................................. 356/301, 72–73
See application file for complete search history.

(56) References Cited

U.S. PATENT DOCUMENTS 5,414,258 A 5/1995 Liang
6,621,574 B1 9/2003 Forney et al.
(Continued)

FOREIGN PATENT DOCUMENTS

CN 101614667 A 12/2009
CN 201819884 U 5/2011
JP 2009103651 A 5/2009

OTHER PUBLICATIONS

Chinese Search Report in Chinese patent application No. 2010/10219542.X, dated Aug. 31, 2012.
(Continued)

*Primary Examiner* — Abdullahi Nur
(74) *Attorney, Agent, or Firm* — Marshall, Gerstein & Borun LLP

(57) ABSTRACT

A Raman spectrum detection system including a light source for emitting excitation light that excites a detected object to emit Raman light; an external light path system for irradiating light emitted from the light source on the detected object and collecting the Raman light emitted by the detected object; a light detection device for receiving the Raman light collected by the external light path system and detecting the Raman light to obtain spectrum data thereof; a control device for controlling the excitation light source to provide the excitation light, controlling the light detection device to detect the Raman light, receiving the spectrum data output from the light detection device, and analyzing said spectrum data to identify the detected object; and an automatic calibration device for holding the standard sample and for automatically calibrating the system.

10 Claims, 4 Drawing Sheets

(56) References Cited

U.S. PATENT DOCUMENTS

| | | | | |
|---|---|---|---|---|
| 7,518,710 B2* | 4/2009 | Gao et al. | ............ | 356/73 |
| 2004/0160601 A1 | 8/2004 | Womble et al. | | |
| 2006/0017922 A1 | 1/2006 | Lewis et al. | | |
| 2009/0323057 A1 | 12/2009 | Chen et al. | | |

OTHER PUBLICATIONS

Supplementary European Search Report in European Patent Application No. EP10853414, dated May 22, 2014.

* cited by examiner idle state detection state

METHOD FOR AUTOMATICALLY CALIBRATING A RAMAN SPECTRUM DETECTION SYSTEM AND RAMAN SPECTRUM DETECTION SYSTEM

CROSS-REFERENCE TO RELATED APPLICATIONS

This is the U.S. national phase of International application No. PCT/CN2010/002159, filed Dec. 24, 2010, which claims the benefit of Chinese patent application No. 10219542.X, filed Jun. 25, 2010.

TECHNICAL FIELD

The present disclosure relates to a Raman spectrum detection system and a method for automatically calibrating the Raman spectrum detection system. The present disclosure also relates to a method for detecting an object using a Raman spectrum detection system with self-calibration.

BACKGROUND ART

Scattering occurs when light irradiates a substance. During scattering, the wavelengths of most of the scattered light do not change, and the scattering radiation without any wavelength change is called Rayleigh scattering; but the wavelengths of a small part of the scattered light will increase or decrease, and the scattering radiation with wavelength change is called Raman scattering, whose corresponding spectrum is called Raman spectrum. The Raman spectrum is a vibration spectrum of molecules. By detecting the Raman spectrum of a substance, it is possible to know what the detected substance is or which component it contains, so the Raman spectrum can be used as the "fingerprint" for identification of substances. In view of this, the Raman spectrum has important application in such fields as medicine, food security, cultural relic and jewel authentication, and security check, etc. Meanwhile, with the more and more wide application of the Raman spectrum in these fields, there is a need for a Raman spectrometer capable of fast on-site detection to be adapted for different environments of various occasions of application. However, the characteristics of the laser light for exciting the Raman scattering of the substance, such as frequency and power, etc., will change with the environment temperature and the time of use, thus the detected Raman spectrum will also change. In addition, with respect to a Raman spectrometer that is frequently moved, the light path structure or the like of the system may be changed because of shaking, etc. during transportation and using, resulting in changes in the excitation efficiency and the signal collection efficiency for the excited Raman light, thus the Raman spectrum might change when the system detects the same sample at different time and in different environment. Raman spectrometers for scientific research mostly use a laser having stable frequency and power as the excitation light source, and have strict requirement on the operating environment. However, a laser having stable frequency and power is expensive, which hinders the popularization of the Raman spectrometer. Even if the laser with stable frequency and power is used, the power thereof will attenuate after using for some time, which will result in uncertain results of detection.

SUMMARY OF THE DISCLOSURE

Therefore, the object of the present disclosure is to provide a Raman spectrum detection system and a method for eliminating influences on the detected Raman spectrum caused by changes in the system performance resulted from changes in the environment factors and key components.

According to one aspect of the present disclosure, a Raman spectrum detection system is provided, which comprises: a light source for emitting excitation light that excites a detected object to emit Raman light; an external light path system for irradiating light emitted from the light source on the detected object and collecting the Raman light emitted by the detected object; a light detection device for receiving the Raman light collected by the external light path system and detecting said Raman light to obtain spectrum data thereof; a control device for controlling the excitation light source to provide the excitation light, controlling the light detection device to detect the Raman light, receiving the spectrum data output from the light detection device, and analyzing said spectrum data to identify the detected object; and an automatic calibration device for automatically calibrating the Raman spectrum detection system.

According to a preferred embodiment of said aspect of the present disclosure, the automatic calibration device comprises a standard sample and a restoring and fixing unit for said standard sample.

According to a preferred embodiment of said aspect of the present disclosure, the restoring and fixing unit is a spring.

According to a preferred embodiment of said aspect of the present disclosure, the control device further comprises a calibration unit for determining current characteristics of the system by analyzing the Raman spectrum data of the standard sample received from the light detection device, and calibrating the Raman spectrum data of the detected object based on said current characteristics.

According to a preferred embodiment of said aspect of the present disclosure, the external light path system comprises a reflector which reflects the excitation light from the light source; a filter which reflects the excitation light reflected by the reflector and allows transmission of the Raman light having a wavelength longer than that of said excitation light; a collecting lens which focuses the excitation light from the filter on the detected object and collects the Raman light emitted by the detected object; a converging lens, which focuses the Raman light collected by the collecting lens on the light detection device.

According to a preferred embodiment of said aspect of the present disclosure, the filter is a dichroic mirror or a notch filter.

According to a preferred embodiment of said aspect of the present disclosure, an alarm device is also comprised for receiving the result of identification from the control device and outputting a prompt or alarm.

According to a preferred embodiment of said aspect of the present disclosure, the characteristics comprise frequency and power of the light source and excitation efficiency and signal collection efficiency of the external light path system.

According to another aspect of the present disclosure, a method for detecting an object using the above-mentioned Raman spectrum detection system is provided, which comprises the steps of automatically calibrating the system using a standard sample, controlling the excitation light to irradiate an object to excite the object to emit Raman light, detecting the Raman light to obtain spectrum data of said Raman light, and analyzing said spectrum data to identify said object.

According to yet another aspect of the present disclosure, a method for automatically calibrating the above-mentioned Raman spectrum detection system is provided, which comprises the steps of controlling the excitation light to irradiate the standard sample, before the detected object is detected, so as to excite said standard sample to emit Raman light, receiving said Raman light and obtaining spectrum data of said Raman light, analyzing said spectrum data to determine the current characteristics of the system, and obtaining calibration values of the automatic calibration system by comparing the current characteristics of the system to the pre-stored data.

DETAILED DESCRIPTION

Figure 1:
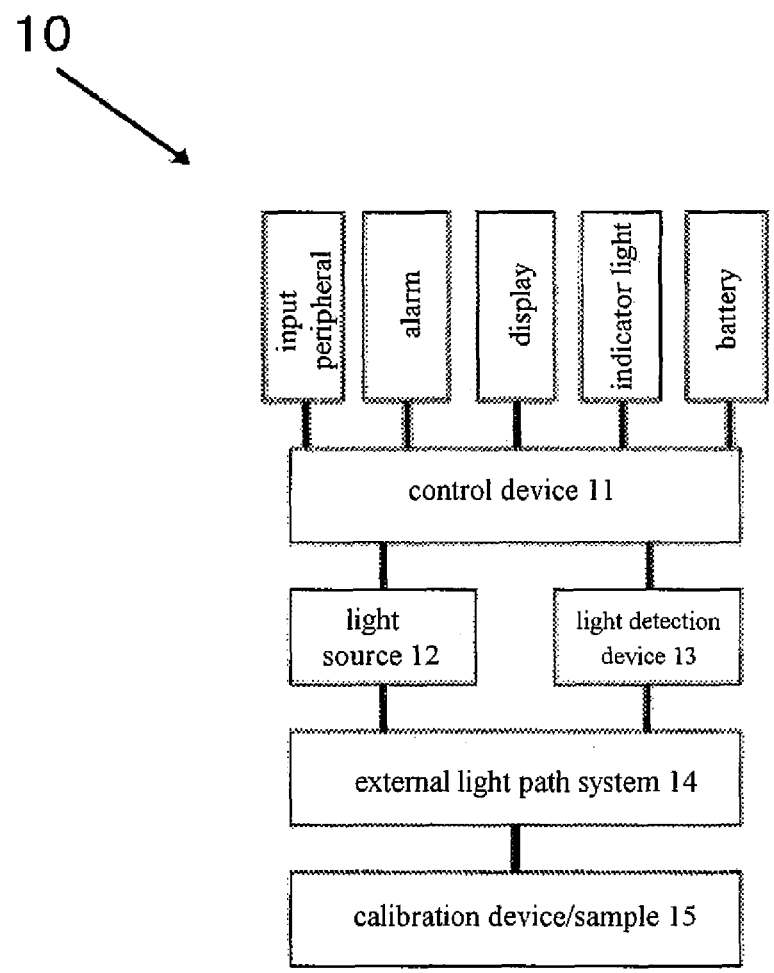
FIG. 1 illustrates schematically the Raman spectrum detection system according to an embodiment of the present disclosure.

FIG. 1 illustrates the Raman spectrum detection system according to an embodiment of the present disclosure, said Raman spectrum detection system being represented, as a whole, by reference sign 10 in FIG. 1

In one embodiment, the Raman spectrum detection system 10 comprises a control device 11, a light source 12, an external light path system 14, a light detection device 13 and a calibration device 15 having a standard sample.

The light source 12 emits, under the control of the control device 11, excitation light that excites the detected object to emit Raman light. In principle, any light source capable of providing excitation light having narrow linewidth, stable frequency and power can be used in the present disclosure. In one embodiment, the light source 12 uses a laser with a central wavelength of 785 nm and emitting collimated parallel light. Of course, a laser having other wavelengths can also be used, for example, a laser having a central wavelength of 532 nm. In this case, the external light path system 14 and the light detection device 13 will be adjusted according to the excitation wavelength.

The excitation light emitted by the light source 12 irradiates on the detected object via the external light path system 14, thereby exciting the detected object to emit Raman light. Said Raman light is collected and transmitted to the light detection device 13 by the external light path system 14. In one embodiment, the external light path system 14 is an optical fiber probe. The light source 12 and the light detection device 13, in this case, may have optical fiber interfaces. In another embodiment, the external light path system 14 is implemented in the form of free space coupling. In this case, the light source 12 outputs collimated parallel light, and the light detection device may have no optical fiber interface.

The light detection device 13 receives the Raman light of the detected object collected by the external light path system 14 and detects said Raman light under the control of the control device 11. In one embodiment, the light detection device 13 is a spectrometer which separates Raman light of different frequencies and acquires signal intensities of Raman light of different frequencies, thereby obtaining Raman spectrum data of the detected object. In another embodiment, said spectrometer has a photoelectric detector which will be described in detail below.

The light detection device 13 transmits the obtained Raman spectrum data of the detected object to the control device 11. In one embodiment, the control device 11 may be a single-chip microcomputer, while in another embodiment, the control device 11 may be a general purpose computer or a computer for industrial use. The control device 11 has an operating system, software and a standard Raman spectrum data base installed, and analyzes and processes the Raman spectrum data transmitted from the light detection device 13. Specifically, the control device 11 uses the standard Raman spectrum data base and a pre-installed pattern identification algorithm to determine whether the received Raman spectrum data is the same as or similar with the Raman spectrum data of prohibited articles such as drugs, exploder, etc. If it is, it will be determined that the detected object is a prohibited article or contains prohibited articles. In this case, the control device 11 can display the result of identification on a display connected to the control device 11 and can send alarm signals through an alarm also connected to the control device 11, said alarm signals being in the form of sound, light, or vibration. On the contrary, if it is determined that the detected object is not a prohibited article or does not contain any prohibited articles, the control device 11 can also display the result of identification on the display and sends a signal of safety through an indicator light also connected to the control device 11. The display may be a touch screen.

Figure 2:
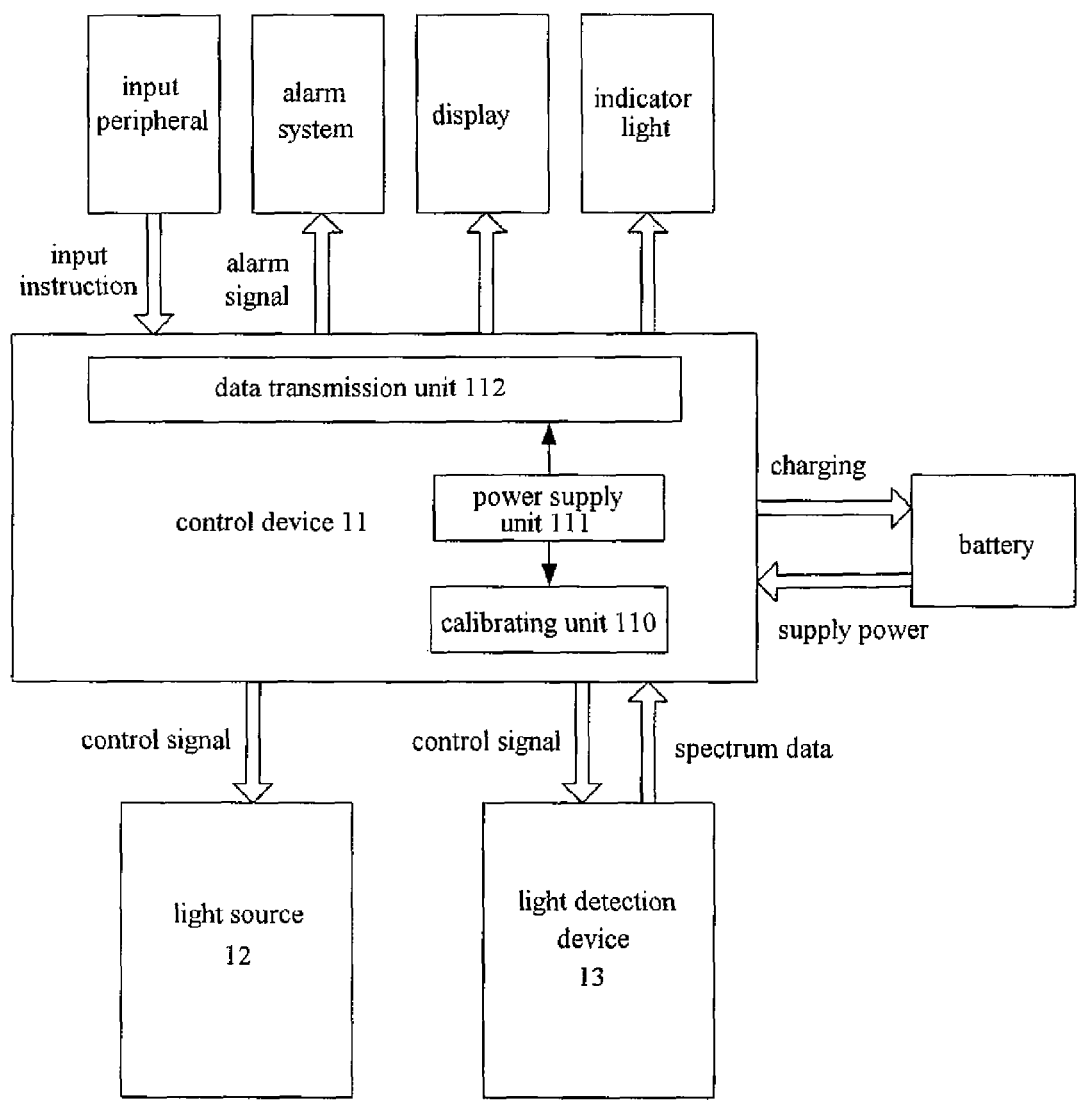
FIG. 2 illustrates schematically an exemplary control device of the Raman spectrum detection system according to an embodiment of the present disclosure.

In one embodiment of the present disclosure, the control device 11 also has a calibration unit which is shown in FIG. 2 as 110. The calibration unit 110 can automatically calculate calibration parameters of the system based on a standard sample, so that the control device 11 can take said calibration parameters into account while analyzing and processing the Raman spectrum data of the detected object. This will be described below in detail.

In addition, the Raman spectrum detection system 10 may further comprise a sample chamber for holding the detected object so as to eliminate the influence of the ambient stray light. The Raman spectrum detection system 10 may further comprise a chargeable battery for supplying the Raman spectrum detection system 10 with power in the case of no external power supply and charging in the case of an external power supply.

FIG. 2 illustrates in detail the control device 11 according to an embodiment of the present disclosure.

In this embodiment, the control device 11 uses a control circuit plate having, for example, an arm 9 chip, which is pre-installed with a WinCE operating system. The control device 11 receives instructions and parameters from an input peripheral, sends control signals to the light source 12 and the light detection device 13, and receives the spectrum data from the light detection device 13. After identifying the spectrum data, the control device 11 transmits the result of identification to the display and sends alarm signal where necessary. In one embodiment, the input peripheral may be a pushbutton, a switch or a keyboard, which sets the parameters of components of the Raman spectrum detection system 10 by inputting instructions to the control device 11, and transmits operation instructions to the Raman spectrum detection system 10.

In one embodiment, the control device 11 may also have a power supply unit 111 and a data transmission unit 112 as required. The power supply unit 111 is used to convert the external power supply into the power supply needed by the Raman spectrum detection system 10. The power supply unit 111 can also charge the optional battery, which supplies power to the Raman spectrum detection system 10 when there is no external power supply. The data transmission unit 112 is used to receive data input into the Raman spectrum detection system 10 from the outside, and can transmit said data. Said data transmission unit 112 may be a serial interface, a parallel interface, a USB interface, a network interface or a wireless network interface, such as a Bluetooth.

By means of said data transmission unit 112, the Raman spectrum detection systems 10 of the embodiments of the present disclosure and a control center can form a network system for detection. Said control center realizes system database updating and parameter setting, etc. by means of the network communication function of the Raman spectrum detection systems 10. The Raman spectrum detection systems 10 of the embodiments of the present disclosure can transmit the detected data and results to the control center via the network, or export data to a U-disk or other storage devices via the data transmission unit 112, or print the result of detection with a printer connected to the data transmission unit 112.

Figure 3A:
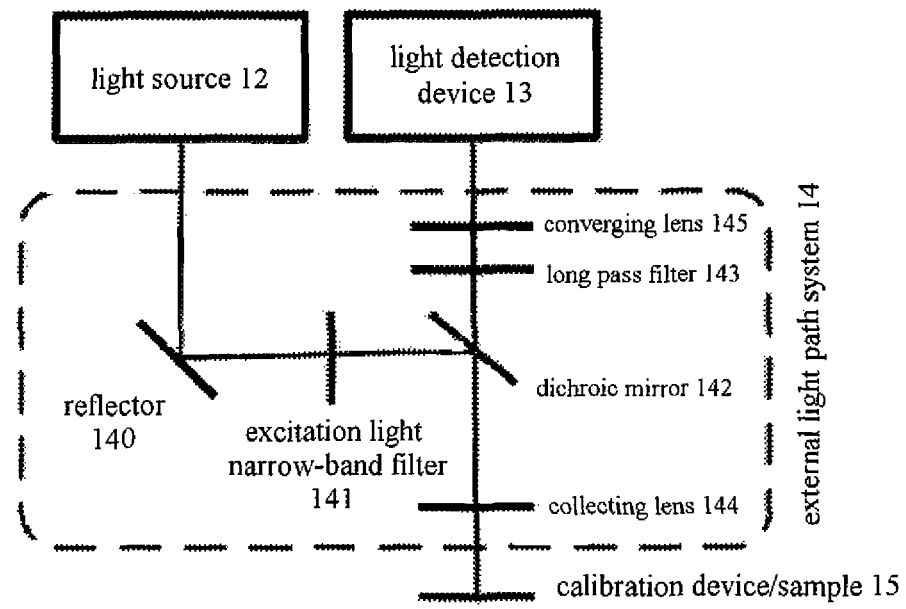
FIG. 3a illustrates schematically an exemplary configuration of the external light path system of the Raman spectrum detection system according to an embodiment of the present disclosure.

FIG. 3a shows schematically an exemplary configuration of the external light path system 14 of the Raman spectrum detection system 11 according to an embodiment of the present disclosure.

In this exemplary configuration, the external light path system 14 is implemented in the form of a free space coupling. Said external light path system 14 comprises a reflector 140, an excitation light narrow-band filter 141, a dichroic mirror 142, a long pass filter 143, a collecting lens 144 and a converging lens 145. The excitation light emitted by the light source 12 that is formed as the laser shown in FIG. 1 is reflected by the reflector 140, and is then reflected by the dichroic mirror 142 after passing through the excitation light narrow-band filter 141. The reflected light is focused, by the collecting lens 144, onto, for example, the detected object placed in the sample chamber. The signal light thereby excited from the detected object is collected by the same collecting lens 144, and is focused onto the light detection device 13, for example, onto the slit of the spectrometer, by the converging lens 145 after passing through the dichroic mirror 142 and the long pass filter 143, thus entering the light detection device 13.

In this example, the excitation light narrow-band filter 141 is used to filter the stray light except for the excitation wavelength in the laser light, the stray light coming mainly from the spontaneous radiation of the laser. The central wavelength of said filter 141 is the same as that of the selected laser. If the stray light of the selected laser does not influence the detection of the Raman spectrum, the excitation light narrow-band filter 141 may not be used.

In this example, the dichroic mirror 142 reflects the excitation light, filters the Rayleigh scattering light having the same wavelength as the excitation light in the signal light, and allows transmission of the Raman light having a wavelength longer than that of the excitation light. The dichroic mirror 142 is preferably a filter having an incident angle of 45 degrees. Of course, the dichroic mirror 142 may also be a filter having other incident angles, for example, about 5 degrees, and when light is incident at said angles, light having the same wavelength with that of the excitation light should be allowed to be reflected and light having a wavelength longer than that of the excitation light should be allowed to be transmitted.

In this example, a long pass filter 143 is preferably used to further filter the Rayleigh scattered light in the signal light. The long pass filter 143 has a high reflectivity for the excitation light wavelength, and has a high transmissivity for light having a wavelength longer than that of the excitation light. The long pass filter may also be replaced by a notch filter, which has a high reflectivity only for light of the wavelength of the excitation light and has a high transmissivity for light of other wavelengths, and the incident angle thereof depends on the operating requirements.

In this example, the collecting lens 144 is preferably a quartz convex lens, which focuses the excitation light onto the detected object, and collects the signal light emitted by the detected object. The quartz convex lens has a minor fluorescent effect so as not to interfere the signal light of the detected object.

In this example, the converging lens 145 is preferably an achromatic lens. The converging lens focuses the signal light onto the light detection device 13, for example, onto the slit of the spectrometer, and the ratio of the focal length thereof to the clear aperture (f/D) is preferably matching the numerical aperture (F#) of the spectrometer to achieve maximum utilization of the signal light.

Figure 3B:
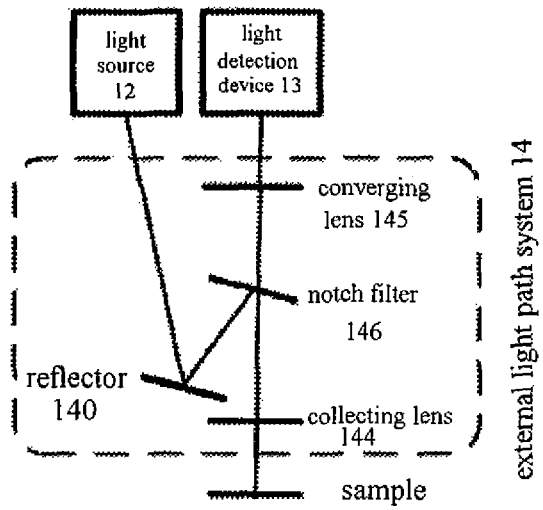
FIG. 3b illustrates schematically another exemplary configuration of the external light path system of the Raman spectrum detection system according to an embodiment of the present disclosure.

FIG. 3b shows schematically another exemplary configuration of the external light path system of the Raman spectrum detection system according to an embodiment of the present disclosure.

The configuration of said example differs from that shown in FIG. 3a in that it uses a notch filter 146 to replace the dichroic mirror 142 and the long pass filter 143 of FIG. 3a. The notch filter 146 is preferably a filter having an incident angle of about 10 degrees.

In the embodiment of the present disclosure, the light detection device 13 is a spectrometer. In the exemplary configurations shown in FIGS. 3a and 3b, the spectrum range of the spectrometer must match the selected excitation light wavelength and be able to cover the Raman spectrum range of the detected object. For example, if the excitation light of 785 nm is selected to detect the Raman peak within 200-2000 cm$^{-1}$ of an detected object, then the spectrum range measurable by the spectrometer must cover 797 nm-932 nm; if the excitation light of 532 nm is selected to detect the Raman peak within 200-2000 cm$^{-1}$ of the same detected object, then the spectrum range measurable by the spectrometer must cover 537 nm-596 nm. In this embodiment, the spectrometer has a photoelectric detector. Said photoelectric detector is preferably a linear array detector or an area array detector, such as a CCD, and the widths of the grating and the slit are selected to enable an identification of the Raman peak of the detected object and a good signal intensity.

Figure 4:
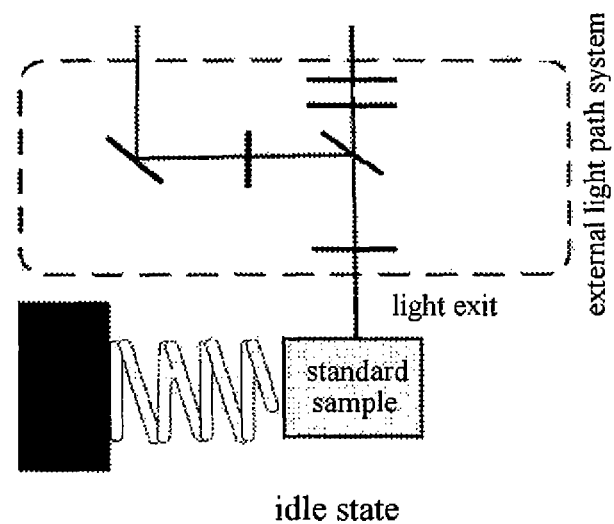
FIG. 4 illustrates schematically an exemplary automatic calibration device of the Raman spectrum detection system according to an embodiment of the present disclosure.
Figure 4:
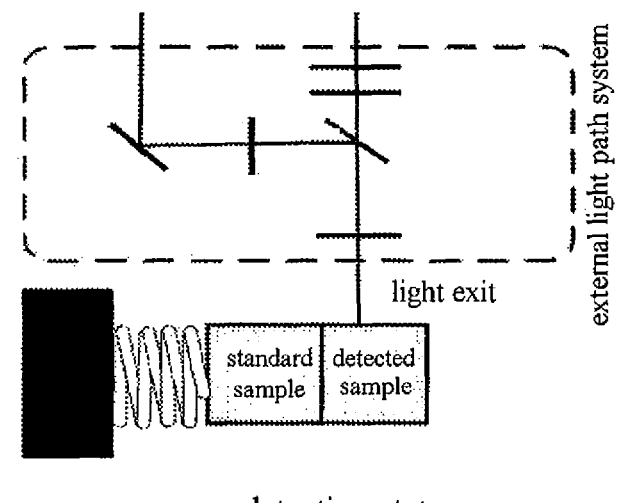

FIG. 4 shows schematically an exemplary automatic calibration device 15 of the Raman spectrum detection system 10 according to an embodiment of the present disclosure.

Said automatic calibration device 15 is, for example, a movable baffle with standard sample coated thereon. Said movable baffle is connected to one end of a spring, and the other end of the spring is fixed, for example, onto the housing of the Raman spectrum detection system 10.

Before detection, the Raman spectrum detection system 10 is in an idle state. At this time, the movable baffle having a standard sample coated thereon is located in the light exit of the system, and the spring is in a balanced position. If an instruction of calibration is input via the input peripheral, then the control device 11 of the Raman spectrum detection system 10 controls the light source 12 to emit light, and the emitted excitation light is irradiated on the standard sample through the external light path system 14. Then the external light path system 14 collects the Raman signal light emitted by the standard sample and transmit it to the light detection device 13 that is formed as a spectrometer. The light detection device 13 detects the light signal to obtain the Raman spectrum data, and transmits said data to the control device 11. The control device 11 analyzes said data to obtain the calibration parameters so as to calibrate other components of the Raman spectrum detection system 10.

In one embodiment, the light detection device 13 detects the Raman spectrum of the standard sample and transmits it to the calibration unit 110 of the control device 11. Said calibration unit 110 automatically identifies the position and strength of the Raman peak of the standard sample, and calculates the differences between the detected peak position and the peak position of the Raman peak of the pre-stored standard sample, which is just the frequency difference between the Raman peak and the real peak of the detected object at the time, and is called frequency calibration value herein. The real frequency of the Raman peak of the detected object can be obtained by subtracting said frequency calibration value from the frequency of the Raman peak of the detected object, thereby realizing the calibration of the Raman peak frequency. The calibration unit 110 also calculates the ratio between the measured peak strength value and the pre-stored peak strength value, which is just the ratio between the Raman peak strength and the real peak strength of the detected object at the time and is called the strength calibration value herein. The real peak strength of the Raman peak of the detected object can be obtained by dividing the Raman peak strength of the detected object by said strength calibration value, thereby realizing the calibration of the Raman peak strength.

During real detection, the detected object is placed at the light exit of the system, for example, at the sample chamber. The detected object pushes away the standard sample, so that the spring is compressed. At this time, the Raman spectrum detection system 10 is in a detecting state and detects the detected object according to the generally known detecting procedure of the Raman spectrometer.

Upon completion of the detection, the detected object is taken away from the light exit of the system. The compressed spring restores to its original shape at this time and pushes back the baffle coated with the standard sample, then the Raman spectrum detection system 10 returns to the idle state.

From descriptions of the embodiments of the present disclosure, those skilled in the art could understand that the disclosed Raman spectrum detection system 10 has a fast automatic calibration function, thus lowering the requirements of the Raman spectrometer, especially the portable Raman spectrometer, on the laser used as the light source, and effectively reducing the cost of the apparatus. Moreover, said automatic calibration function improves the accuracy of detection, improves the adaptability of the Raman spectrometer to the environment, and broadens the range of application of the Raman spectrometer.

The above detailed descriptions should be understood as being illustrative and demonstrative instead of restrictive in all aspects. The scope of disclosure disclosed herein should not be determined by the preferred embodiments, but should be determined by the appended claims. It should be understood that the embodiments illustrated and described herein are only for explaining the principle of the present disclosure, while those skilled in the art could make various modifications without departing from the spirit and scope of the present disclosure.

What is claimed is:

1. A Raman spectrum detection system, comprising:
    a light source for emitting excitation light that excites the detected object to emit Raman light;
    an external light path system for irradiating light emitted from the light source on a detected object and collecting the Raman light emitted by the detected object;
    a light detection device for receiving the Raman light collected by the external light path system and detecting said Raman light to obtain spectrum data thereof;
    a control device for controlling the excitation light source to provide the excitation light, controlling the light detection device to detect the Raman light, receiving the spectrum data output from the light detection device, and analyzing said spectrum data to identify the detected object; and
    an automatic calibration device for automatically calibrating the Raman spectrum detection system,
    wherein the automatic calibration device comprises a standard sample, and the automatic calibration device is arranged at the light exit of the external light path system such that the automatic calibration device receives light from the external light path system and the external light path system collects the Raman light from the standard sample,
    wherein the external light path system comprises:
        a reflector which reflects the excitation light from the light source;
        a filter which reflects the excitation light reflected by the reflector and allows transmission of the Raman light having a wavelength longer than that of said excitation light;
        a collecting lens which focuses the excitation light from the filter onto the detected object and collects the Raman light emitted by the detected object; and
        a converging lens, which focuses the Raman light collected by the collecting lens onto the light detection device, and
    wherein the location and angle of the reflector vary with the angle of the excitation light emitted from the light source to reflect the excitation light emitted by the light source to the filter.

2. The Raman spectrum detection system according to claim 1, characterized in that the automatic calibration device comprises a restoring and fixing unit for the standard sample.

3. The Raman spectrum detection system according to claim 2, characterized in that the restoring and fixing unit is a spring.

4. The Raman spectrum detection system according to claim 2, characterized in that the control device further comprises a calibration unit for determining the current characteristics of the system by analyzing the Raman spectrum data of the standard sample received from the light detection device, and calibrating the Raman spectrum data of the detected object based on said current characteristics.

5. The Raman spectrum detection system according to claim 4, characterized in that the characteristics include frequency and power of the light source and excitation efficiency and signal collection efficiency of the external light path system.

6. The Raman spectrum detection system according to claim 1, characterized in that the filter is a dichroic mirror or a notch filter.

7. The Raman spectrum detection system according to claim 1, characterized by further comprising an alarm device for receiving the result of identification from the control device and outputting a prompt or alarm.

8. A method for detecting an object using the Raman spectrum detection system according to claim 1, comprising the steps of automatically calibrating the excitation light using a standard sample;
controlling the excitation light to irradiate the object to excite the object to emit Raman light;
detecting the Raman light to obtain spectrum data of said Raman light; and
analyzing said spectrum data to identify said object,
wherein the step of controlling the excitation light further comprises adjusting the location and angle of the reflector when the angle of the excitation light emitted from the light source varies so that the excitation light emitted by the light source is reflected by the reflector to the filter.

9. A method for automatically calibrating a Raman spectrum detection system according to claim 1, comprising the steps of
controlling the excitation light to irradiate a standard sample, before the detected object is detected, so as to excite said standard sample to emit Raman light;
receiving said Raman light and obtaining spectrum data of said Raman light;
analyzing said spectrum data to determine the current characteristics of the system;
obtaining calibration values for automatically calibrating the system by comparing the current characteristics of the system to the pre-stored data,
wherein the step of controlling the excitation light further comprises adjusting the location and angle of the reflector when the angle of the excitation light emitted from the light source varies so that the excitation light emitted from the light source is reflected by the reflector to the filter.

10. The method according to claim 9, characterized in that the characteristics include frequency and power of the light source and excitation efficiency and signal collection efficiency of the external light path system.

\* \* \* \* \*